US005643848A

United States Patent [19]

Lawson et al.

[11] Patent Number: 5,643,848

[45] Date of Patent: *Jul. 1, 1997

[54] SOLUBLE ANIONIC POLYMERIZATION INITIATORS AND PRODUCTS THEREFROM

[75] Inventors: David F. Lawson, Uniontown; James E. Hall, Mogadore, both of Ohio; Yoichi Ozawa, Kodaira, Japan

[73] Assignee: Bridgestone Corporation, Tokyo, Japan

[*] Notice: The term of this patent shall not extend beyond the expiration date of Pat. No. 5,578,542.

[21] Appl. No.: 433,110

[22] Filed: May 3, 1995

Related U.S. Application Data

[63] Continuation-in-part of Ser. No. 220,629, Mar. 30, 1994, Pat. No. 5,578,542, which is a continuation of Ser. No. 968,929, Oct. 30, 1992, abandoned.

[51] Int. Cl.$^6$ ................. C08F 4/08; C07D 295/00; C07D 487/08

[52] U.S. Cl. ................. 502/167; 502/150; 502/172; 526/180; 526/204; 540/450; 540/470; 540/477; 540/484; 544/358; 546/184; 548/400; 252/182.12

[58] Field of Search ................. 526/180, 204; 252/182.12; 502/152, 157, 167, 150, 172, 200; 540/450, 470, 477, 484; 544/358; 546/184; 548/400

[56] References Cited

U.S. PATENT DOCUMENTS

| | | | |
|---|---|---|---|
| 2,849,432 | 8/1958 | Kibler et al. | 260/94.2 |
| 3,109,871 | 11/1963 | Zalinski et al. | 260/85.1 |
| 3,177,190 | 4/1965 | Hsieh | 260/94.2 |
| 3,178,398 | 4/1965 | Strobel et al. | 260/85.1 |
| 3,240,772 | 3/1966 | Natta et al. | 260/88.7 |
| 3,290,277 | 12/1966 | Anderson et al. | 260/88.2 |
| 3,317,918 | 5/1967 | Foster | 260/83.7 |
| 3,326,881 | 6/1967 | Uraneck et al. | 260/94.6 |
| 3,331,821 | 7/1967 | Strobel | 260/83.7 |
| 3,393,182 | 7/1968 | Trepka | 260/79.5 |
| 3,426,006 | 2/1969 | Nützel et al. | 260/83.5 |
| 3,439,049 | 4/1969 | Trepka | 260/624 |
| 3,652,456 | 3/1972 | Naylor | 252/431 |
| 3,856,877 | 12/1974 | Otsuki et al. | 260/677 R |
| 3,935,177 | 1/1976 | Müller et al. | 260/84.7 |
| 4,015,061 | 3/1977 | Schulz et al. | 526/178 |
| 4,026,865 | 5/1977 | Uraneck et al. | 260/42.32 |
| 4,085,265 | 4/1978 | Otsuki et al. | 526/49 |
| 4,247,418 | 1/1981 | Halasa et al. | 252/431 N |
| 4,316,001 | 2/1982 | Boileau et al. | 528/14 |
| 4,383,085 | 5/1983 | Fujimaki et al. | |
| 4,414,372 | 11/1983 | Farnham et al. | 526/190 |
| 4,429,091 | 1/1984 | Hall | 526/181 |
| 4,476,240 | 10/1984 | Hall et al. | 502/155 |
| 4,478,953 | 10/1984 | Yuki et al. | 502/155 |
| 4,515,922 | 5/1985 | Sakakibara et al. | 525/99 |
| 4,614,771 | 9/1986 | Watanabe et al. | 525/351 |
| 4,616,069 | 10/1986 | Watanabe et al. | 525/370 |
| 4,647,634 | 3/1987 | Jalics | 526/174 |
| 4,677,153 | 6/1987 | Kitahara et al. | 524/552 |
| 4,734,461 | 3/1988 | Roggero et al. | 525/293 |
| 4,735,994 | 4/1988 | Rogger et al. | 525/279 |
| 4,736,003 | 4/1988 | Schneider et al. | 526/190 |
| 4,791,174 | 12/1988 | Bronstert et al. | 525/274 |
| 4,816,520 | 3/1989 | Bronstert | 525/285 |
| 4,835,209 | 5/1989 | Kitagawa et al. | 524/507 |
| 4,843,120 | 6/1989 | Halasa et al. | 525/53 |
| 4,894,409 | 1/1990 | Shimada et al. | 524/492 |
| 4,914,147 | 4/1990 | Mouri et al. | 524/495 |
| 4,931,376 | 6/1990 | Ikematsu et al. | 526/164 |
| 4,935,471 | 6/1990 | Halasa et al. | 525/359.1 |
| 4,978,754 | 12/1990 | Ibi et al. | 544/176 |
| 5,066,729 | 11/1991 | Stayer, Jr. et al. | 525/315 |
| 5,112,929 | 5/1992 | Hall | 526/181 |
| 5,115,035 | 5/1992 | Shiraki et al. | 525/314 |
| 5,149,457 | 9/1992 | Smith | 252/182.12 |
| 5,153,159 | 10/1992 | Antkowiak et al. | 502/155 |
| 5,173,209 | 12/1992 | Smith, Jr. et al. | 252/182.14 |
| 5,238,893 | 8/1993 | Hergenrother et al. | 502/155 |
| 5,248,737 | 9/1993 | Sivak et al. | 525/384 |
| 5,292,790 | 3/1994 | Shimizu et al. | 524/496 |
| 5,329,005 | 7/1994 | Lawson et al. | 526/180 X |
| 5,332,810 | 7/1994 | Kitamura et al. | 540/450 |
| 5,393,721 | 2/1995 | Kitamura et al. | 502/154 |

FOREIGN PATENT DOCUMENTS

| | | |
|---|---|---|
| 0 067 111 A2 | 5/1982 | European Pat. Off. |
| 0 180 141 A1 | 10/1985 | European Pat. Off. |
| 0 207 565 A1 | 6/1986 | European Pat. Off. |
| 0 264 506 A1 | 10/1986 | European Pat. Off. |
| 0 282 437 A2 | 3/1988 | European Pat. Off. |
| 0 290 883 A1 | 4/1988 | European Pat. Off. |
| 0 316 255 A2 | 10/1988 | European Pat. Off. |
| 0 451 603 A2 | 3/1991 | European Pat. Off. |
| 2 250 774 | 11/1974 | France . |
| 138 070 | 10/1979 | Germany . |
| 247455 | 3/1986 | Germany . |
| 54-65788 | 11/1977 | Japan . |
| 59-164308 | 9/1984 | Japan . |
| 2 117 778 | 3/1983 | United Kingdom . |

OTHER PUBLICATIONS

Hackh's Chem. Dictionary (4th ed.) McGraw–Hill, N.Y., N.Y., p. 27 (1969).

"Anionic Polymerization Intiators Containing Protected Functional Groups. II." by Schulz et al., *Journal of Polymer Science: Polymer Chemistry Edition*, vol. 15, pp. 2401–2410 (1977).

"Bifunctional anionic intiators: A critical study and overview" by Bandermann et al., *Makromol. Chem* 186, pp. 2017–2024 (1985).

(List continued on next page.)

*Primary Examiner*—Fred Teskin
*Attorney, Agent, or Firm*—Daniel N. Hall

[57] ABSTRACT

An acyclic alkane soluble anionic polymerization initiator includes a mixture of from about 90 to about 10 parts by weight of a lithio amine having the general formula $A_1Li$ and from about 10 to about 90 parts by weight of at least one other lithio amine having the general formula $A_2Li$. $A_1$ and $A_2$ are selected from the dialkyl, alkyl, cycloalkyl and dicycloalkyl amine radicals and cyclic amine radicals. There is also provided a method of forming a mixture of anionic polymerization initiators, a functionalized polymer and a method of forming a functionalized polymer.

4 Claims, No Drawings

OTHER PUBLICATIONS

"Butadiene–Styrene Copolymerization Initiated by n–BuLi/THF/t–AmOK", by Lehong et al., *Journal of Applied Polymer Science*, vol. 44, pp. 1499–1505 (1992).

"6001 Chemical Abstracts", vol. 91, p. 59 (1979).

"Copolymerization of Butadiene and Styrene by Initiation with Alkyllithium and Alkai Metal tert–Butoxides" by Wofford et al., *Journal of Polymer Science: Part A–1*, vol. 7, pp. 461–469 (1969).

"Lithium Amide Catalyzed Amine–Olefin Addition Reactions" by Schlott et al., *J. Org. Chem.*, vol. 37, No. 26, pp. 4243–4245 (1972).

"New perfectly difunctional organolithium initiators for block copolymer synthesis: Synthesis of dilithium initiators in the absence of polar additives", by Guyot et al., *Polymer*, vol. 22 (1981).

"Polymerization of Unsaturated Compounds in the Presence of Lithium Diethylamide" by Vinogradov et al., *Polymer Science U.S.S.R.*, vol. 4, pp. 1568–1572 (1963).

"Ortho Lithiation via a Carbonyl Synthon" by Harris et al., *J. Org. Chem.*, vol. 44, No. 12, pp. 2004 & 2006 (1979).

"Preparation and Reactions of Trialkyltinlithium" by Tamborski et al., pp. 237–239, Jan. 1963.

"Preparation of Some Trialkyltin–lithium Compounds" by Gilman et al., *J. Am. Chem. Soc.* 75, pp. 2507–2509 (1953).

"Some Reactions of Tributyl– and Triphenyl–stannyl Derivatives of Alkali Metals" by Blake et al., *J. Chem. Soc.*, pp. 618–622, (1961).

"Specific Functionalization of Polymers by Carboxyl Groups" by Broze et al., *Makromol. Chem.* 179, pp. 1383–1386 (1978).

"Stereospecific Addition Reaction Between Butadiene and Amines" by Imai et al., *Tetrahedron Letters No.* 38, pp. 3317–3520 (1971).

"Studies of the Anionic Polymerization of Phenyl Vinyl Sulfoxide and Its Copolymer with Styrene" by Kanga et al. *Macromolecules* 23, pp. 4235–4240 (1990).

"Synthesis of New Monomers by Addition Reactions of Diethylamine to 1,4–Divinylbenzene Catalyzed by Lithium Diethylamide" by Tsuruta et al., *Makromol. Chem.* 177, pp. 3255–3263 (1976).

"The Microstructure of Butadiene and Styrene Copolymers Synthesized with n–BuLi/THF/t–AmOK" by Lehong et al., *Journal of Applied Polymer Science*, vol. 44, pp. 1507–1511 (1992).

"Thermal Elimination of Poly(phenyl vinyl sulfoxide) and Its Polystyrene Block Copolymers" by Kanga et al., *Macromolecules* 23, pp. 4241–4246 (1990).

"Metalations of Benzyldimethylamine and Related Amines with n–Butyllithium in Ether. Deuteration to Form Ring and Side–chain Derivatives" by Jones et al., *J. Org. Chem.* 23, 663 (Mar. 1963) pp. 663–665.

"B–Lithioeamines, New Reagents for Synthesis", by L. Duhamel, J–M Poirer, *J. Am. Chem. Soc.*, 99:25, 8356–7 (1977).

One page translation of Japanese Abstract, Japanese Patent Application 87–180892/26.

One page Derwent Abstract of Japanese Patent JP54065788.

"3–Dimethylaminopropyl–Lithium—An Analytical and Kinetic Investigation of a New Initiator System for Polymer Synthesis" by Eisenbach et al., *European Patent Journal*, vol. 11, pp. 699–704 (1975).

"A Bifunctional Anionic Initiator Soluble in Non–polar Solvents" by Beinert et al., *Makromol. Chem* 179, pp. 551–555 (1978).

"An improved synthesis of p–dimethylaminophenyl––lithium" by Hallas et al., *Chemistry and Industry*, p. 620 (1969).

"Anionic Polymerization. VII Polymerization and Copolymerization with Lithium Nitrogen–Bonded Initiator" by Cheng, *American Chemical Society*, pp. 513–528 (1981).

"Anionic Polymerization Initiators Containing Protected Functional Groups and Functionally Terminated Diene Polymers" by Schulz et al., *Journal of Polymer Science: Polymer Chemistry Edition*, vol. 12, pp. 153–166 (1974).

"Anionic Polymerization Initiated by Diethylamide in Organic Solvents. I. The Use of Lithium Diethylamide as a Polymerization Catalyst and the Effect of Solvent Type on the Polymerization of Isoprene and Styrene" by Angood et al., *Journal of Polymer Science: Polymer Chemistry Edition*, vol. 11, pp. 2777–2791 (1973).

Riddick et al., *Organic Solvents* (3rd ed.) vol. II, Wiley––Interscience, N.Y., 52–3 (1970).

SOLUBLE ANIONIC POLYMERIZATION INITIATORS AND PRODUCTS THEREFROM

RELATED APPLICATION

The subject application is a continuation-in-part of pending U.S. patent application Ser. No. 08/220,629 filed on Mar. 30, 1994, now U.S. Pat. No. 5,578,542, which in turn is a continuation of U.S. patent application Ser. No. 07/968,929 filed on Oct. 30, 1992, and now abandoned.

TECHNICAL FIELD

The subject invention relates to anionic polymerization resulting in diene homo- and copolymer elastomers. More particularly, the present invention relates to polymerization employing soluble lithio amine initiators. Specifically, the invention relates to an initiator which is a mixture of at least two different lithio amines, wherein their mixture confers solubility. The initiator is soluble in acyclic alkane solvents, and reproducibly polymerizes monomers in a controllable manner to products with a narrow molecular weight distribution range and other desirable properties.

BACKGROUND ART

When conducting polymerizations on a commercial basis, it is important to utilize process conditions and components which will allow the molecular weight of the end products to be narrowly and reproducibly defined. The characteristics of a given polymer and its usefulness are dependent, among other things, upon its molecular weight. Hence, it is desirable to be able to predict with some certainty the molecular weight of the end product of the polymerization. When the molecular weight is not narrowly definable, or is not reproducible on a systematic basis, the process may not be commercially viable.

In the art, it is desirable to produce elastomeric compounds exhibiting reduced hysteresis characteristics. Such elastomers, when compounded to form articles such as tires, power belts and the like, will show an increase in rebound, a decrease in rolling resistance and will have less heat build-up when subjected to mechanical stresses.

A major source of hysteretic power loss has been established to be due to the section of the polymer chain from the last cross link of the vulcanizate to an end of the polymer chain. This free end cannot be involved in an efficient elastically recoverable process, and as a result, any energy transmitted to this section of the cured sample is lost as heat. It is known in the art that this type of heat loss can be reduced by preparing higher molecular weight polymers which necessarily have fewer end groups per given weight. However, this procedure is not always useful because processability of the rubber with compounding ingredients and during shaping operations decreases rapidly with increasing molecular weight.

U.S. Pat. No. 5,149,457 describes the use of mixtures of certain lithio amines to confer solubility in aromatic solvents. However, the use of aromatic solvents is often undesirable for anionic polymerizations. Moreover, the lithium amides or lithio amines described in that patent are either unsuitable or undesirable as anionic polymerization initiators, or will not give products with reduced hysteresis characteristics.

It is difficult to obtain consistent properties, such as a reduction in hysteresis characteristics, if the polymer cannot be controllably reproduced in a narrow molecular weight distribution range. See, for example, U.S. Pat. No. 4,935,471, in which some polymers are prepared with a heterogeneous mixture of certain secondary amines, including lithium pyrrolidide. Polymers made in this manner have widely varying molecular weights, broad polydispersities, and their functional terminations tend to be erratic, giving rise to poorly reproducible hysteresis reduction results.

A major drawback with many of these known anionic lithio amine initiators, is that they are not soluble in acyclic alkanes, such as hexane. Polar solvents have heretofore been employed including the polar organic compounds, especially ethers such as dimethyl or diethyl ether, as well as tetrahydrofuran, diethylene glycol methyl ether (diglyme).

The present invention provides novel, acyclic alkane soluble initiators, useful to initiate an anionic polymerization. The invention provides for the incorporation of two separate functionalities from the initiator at two or more ends of separate polymer chains. The invention also provides for efficient, controllable and reproducible polymerizations, with the preparation of well defined end-products of a relatively narrow molecular weight distribution range and having desired hysteretic properties.

DISCLOSURE OF THE INVENTION

It is therefore, an object of the present invention to provide anionic polymerization initiators which are soluble in acyclic alkanes.

It is a further object of the present invention to provide a method of forming a functionalized polymer from such an anionic polymerization initiator.

It is still a further object of the invention to provide an initiator which will reproducibly polymerize a monomer or monomers within a narrow, predictable molecular weight range.

It is an additional object of the invention to provide such an initiator which will allow for the incorporation of two separate functional groups onto separate ends of the resulting polymers.

It is another object of the present invention to provide elastomers formed with such a polymerization initiator.

It is also an object of certain embodiments of the present invention to provide diene polymers having reduced hysteresis characteristics.

It is a further object of the present invention to provide vulcanizable elastomeric compounds.

Still another object of the present invention is to provide an improved tire formed at least in part, from an elastomer as above.

These and other objects together with the advantages thereof over the existing art, which shall become apparent from the specification which follows, are accomplished by the invention as hereinafter described and claimed.

In general, there is provided according to the invention, an acyclic alkane soluble anionic polymerization initiator for the preparation of a polymer having reduced hysteresis characteristics. The initiator is a mixture comprising from about 90 to about 10 parts by weight of a lithio amine having the general formula $A_1Li$ and from about 10 to about 90 parts by weight of at least one other lithio amine having the general formula $A_2Li$. $A_1$ and $A_2$ are different and are independently selected from the group consisting of cyclic amine radicals having the general formula

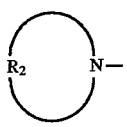

where $R_2$ is selected from the group consisting of a divalent alkylene, bicycloalkane, substituted alkylene, oxy- or N-alkylamino-alkylene group having from about 3 to about 16 methylene groups.

There is also provided according to the invention, a method of preparing an acyclic alkane soluble, anionic polymerization initiator for the preparation of a polymer having reduced hysteresis characteristics. The method comprises the steps of forming a solution of a first amine and at least one other amine in an anhydrous, aprotic, acyclic alkane solvent; adding an organolithium reagent to the solution and allowing said organolithium reagent to react with the amines. Each of the amines are selected from the group consisting of cyclic amines having the general formula

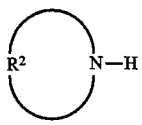

where $R_2$ is as shown hereinabove.

PREFERRED EMBODIMENTS FOR CARRYING OUT THE INVENTION

As will become apparent from the description which follows, the present invention provides novel polymerization initiators which are mixtures soluble in acyclic alkanes such as hexane, pentane, heptane, octane, their alkylated derivatives, mixtures thereof and the like. A initiator is considered to be soluble herein if it is soluble up to about 1 molar concentration at room temperature, as demonstrated by a lack of observable precipitate. Some useful initiators according to the invention are soluble at lower and some at higher concentrations. It has also been discovered herein that certain vulcanizable elastomeric compounds and articles thereof based upon functionalized polymers formed using such an initiator mixture, exhibit useful properties, such as for example, reproducible relatively narrow molecular weight ranges. Furthermore, each of the resulting polymers contains a functionality from one of the components of the initiators, which functionality is useful for example, in improving hysteresis properties, that is, reducing hysteretic loss.

While the initiators of the present invention are soluble in acyclic alkane solvents, it will be appreciated that the use of the initiators in other solvent systems is also within the scope of the invention, as will be further described hereinbelow.

The initiator according to the invention preferably consists essentially of a metal amide which may or may not be soluble in an acyclic alkane solvent, and one or more other metal amides which also may or may not be soluble in an acyclic alkane solvent. Preferably, the metal amides are lithium amides (also called lithio amines), and the present invention will be exemplified hereinbelow with respect to lithium, it being understood that other metal amides are within the scope of the invention.

The initiator has the general formula $xA_1Li \cdot yA_2Li$, where $x+y=1$ and both x and y range from about 0.1 to about 0.9, and preferably from 0.3 to about 0.7. That is, in the broad embodiment, the initiator contains from about 90 to about 10 parts by weight of $A_1Li$ and from about 10 to about 90 parts by weight of $A_2Li$.

The $A_1$ and $A_2$ components in each of the amines of the initiator, represent an amine functionality to be incorporated into the resulting polymer. For example, $A_1$ and $A_2$ may be selected from the group consisting of dialkyl, alkyl, cycloalkyl and dicycloalkyl amine radicals having the general formula

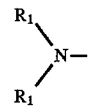

and cyclic amine radicals having the general formula

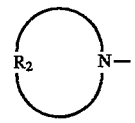

Each $R_1$ is independently selected from the group consisting of alkyls, cycloalkyls or aralkyls having from 1 to about 12 carbon atoms, and $R_2$ is selected from the group consisting of a divalent alkylene, bicycloalkane, substituted alkylene, oxy- or N-alkylamino-alkylene group having from about 3 to about 16 methylene groups.

Exemplary $R_1$ groups include methyl, ethyl, butyl, octyl, cyclohexyl, 3-phenyl-1-propyl, isobutyl and the like. Exemplary $R_2$ groups include tetramethylene, hexamethylene, oxydiethylene, N-alkylazadiethylene and the like. $R_2$ may be bicyclic, such that two methylene groups therein are bridged to form a bicycloalkane, such as 1,3,3-trimethyl-6-azabicyclo [3.2.1] octane. By "bridged" it is understood to mean that two non-adjacent methylene groups in a larger ring are connected, either by bonding directly or through an alkylene group having one or more methylene groups, thus forming a bicyclic structure of smaller rings.

It has been found that when one or both R1 and $R_2$ are both t-butyl groups, both isopropyl groups or the like, the resulting polymerizations are slow, presumably due to hindrance around the nitrogen at the initiation site. Hence, in a preferred embodiment of the invention, the carbon atoms in $R_1$ and $R_2$ bonded directly to the nitrogen in the amine radical, are also bonded to at total of at least three hydrogen atoms.

For example, as long as $A_1$ and $A_2$ are different they may each be a derivative of pyrrolidine; piperidine; piperazine; perhydroazepine, also known as hexamethyleneimine (HMI); 3,3,5-trimethyltetrahydroazepine, also known as trimethylhexamethyleneimine (THMI); 1-azacyclooctane including bicyclics such as perhydroisoquinoline, perhydroindolene; azacyclotridecane; azacycloheptadecane; azacycloheptadec-9-ene; azacycloheptadec-8-ene; and the like. $A_1$ and $A_2$ may each also be derived from di-n-propylamine, diisobutylamine, ethylamine, or n-butylamine. Pyrrolidine, perhydroazepine and 1-azacyclooctane are preferred for forming the metal amides in the mixture.

Preferred $A_1$ and $A_2$ components for the amine precursor of the metal amides include hexamethyleneimine, 1,3,3-trimethyl-6-azabicyclo [3.2.1] octane, diisobutylamine, pyrrolidine, 1-azacyclooctane, 3,3,5-trimethyltetrahydroazepine.

As stated hereinabove, some of the metal amides may not each be themselves soluble (as the term is used herein) in acyclic alkanes. For example, lithium pyrrolidide, lithium hexamethyleneimine and lithium azacyclooctane are not soluble in hexane, while lithium diisobutylamide is soluble in hexane. One of the unexpected results of the invention, is that such otherwise non-soluble metal amides are rendered soluble when mixed with other metal amides, as will be exemplified hereinbelow.

The initiator according to the present invention can be formed by preparing a mixture of the amine components $A_1H$ and $A_2H$, in an anhydrous, aprotic solvent, such as hexane. To this solution is then added an organolithium reagent in the same or a similar solvent. That is, an acyclic alkane soluble mixture of anionic polymerization initiators is prepared, according to one aspect of the invention, by forming a solution of a first functionalizing agent and at least one other functionalizing agent in an anhydrous, aprotic solvent, and adding an organolithium reagent to the solution. The organolithium reagent has the general formula RLi where R is selected from the group consisting of alkyls, cycloalkyls, alkenyls, aryls and aralkyls having from 1 to about 20 carbon atoms and short chain length low molecular weight polymers from diolefin and vinyl aryl monomers having up to about 25 units. Typical alkyls include n-butyl, s-butyl, methyl, ethyl, isopropyl and the like. The cycloalkyls include cyclohexyl, menthyl and the like. The alkenyls include allyl, vinyl and the like. The aryl and aralkyl groups include phenyl, benzyl, oligo(styryl) and the like. Exemplary short chain length polymers, also known as "oligomers", include the oligo(butadienyls), oligo (isoprenyls), oligo(styryls) and the like.

The solution of the mixture of amines and the organolithium reagent is allowed to react for from several minutes to 1 to 2 hours or more at ambient temperature (25° to 30° C.), or elevated temperatures up to about 100° C., preferably at less than 50° C., and more preferably at less than 38° C., following which the soluble catalyst is ready for use. Reaction times of about one hour are normally sufficient.

The two amide initiators are mixed in amounts of from about 90 to about 10 parts by weight of the first amide component with from about 10 to about 90 parts by weight of the second amide component. It is preferred that the two amides be mixed at a ratio of from about 30:70 to about 70:30 parts by weight, and more preferably at about 50:50 parts by weight. The amide components are mixed in an excess of an acyclic alkane or hydrocarbon solvent. If more than one second amide component is used, the ratios may be adjusted accordingly. The final concentration of mixed lithium amides may range from very dilute to as high as 1 or 2 molar, depending on the combination of amides used.

As stated above, the initiator mixture thus formed may be employed as to prepare many anionically-polymerized elastomers, e.g., polybutadiene, polyisoprene and the like, and copolymers thereof with monovinyl aromatics such as styrene, alpha methyl styrene and the like, or trienes such as myrcene. Thus, the elastomers include diene homopolymers and copolymers thereof with monovinyl aromatic polymers. Suitable monomers include conjugated dienes having from about 4 to about 12 carbon atoms and monovinyl aromatic monomers having 8 to 18 carbon atoms and trienes. Examples of conjugated diene monomers and the like useful in the present invention include 1,3-butadiene, isoprene, 1,3-pentadiene, 2,3-dimethyl-1,3-butadiene and 1,3-hexadiene, and aromatic vinyl monomers include styrene, a-methylstyrene, p-methylstyrene, vinyltoluene and vinylnaphtalene. The conjugated diene monomer and aromatic vinyl monomer are normally used at the weight ratios of 95-50:5-50, preferably 95-65:5-35.

Polymerization is conducted in an acyclic alkane or hydrocarbon solvent, such as the various pentanes, hexanes, heptanes, octanes, their alkylated derivatives, and mixtures thereof. Other solvents may also be used, including cyclohexane, benzene and the like. In order to promote randomization in copolymerization and to control vinyl content, a polar coordinator may be added to the polymerization ingredients. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed.

Compounds useful as polar coordinators are organic and include tetrahydrofuran, linear and cyclic oligomeric oxolanyl alkanes such as 2-2'-di(tetrahydrofuryl) propane, di-piperidyl ethane, hexamethylphosphoramide, N-N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, the subject matter of which is incorporated herein by reference. Compounds useful as polar coordinators include those having an oxygen or nitrogen hetero-atom and a non-bonded pair of electrons. Other examples include dialkyl ethers of mono and oligo alkylene glycols; "crown" ethers; tertiary amines such as tetramethylethylene diamine (TMEDA); linear THF oligomers and the like.

A batch polymerization is prepared by conventional techniques, and may be begun by charging a blend of monomer(s) and acyclic alkane solvent or other appropriate solvents, to a suitable reaction vessel, followed by the addition of the polar coordinator (if employed) and the mixture of initiator compounds previously described. The reactants are heated to a temperature of from about 20° to about 200° C., and the polymerization is allowed to proceed for from about 0.1 to about 24 hours. A functional amine group is derived from each of the initiator compounds and bonds at the initiation site of one of the growing polymers. Thus, substantially every resulting polymer chain has the general formula $A_1YLi$ or $A_2YLi$ where $A_1$ and $A_2$ are as described above, and Y is a divalent polymer radical which is derived from any of the foregoing diene homopolymers, monovinyl aromatic polymers, diene/monovinyl aromatic random copolymers and block copolymers. The monomer addition at the lithium end causes the molecular weight of the polymer to increase as the polymerization continues.

To terminate the polymerization, and thus further control polymer molecular weight, a polymer modifying agent such as a terminating, coupling or linking agent may be employed. Useful modifying agents include active hydrogen compounds such as water or alcohol, or compounds providing multifunctionality such as, for example, carbon dioxide; tetramethyldiaminobenzophenone; dialkyl- and dicycloalkyl-carbodiimides having from about 5 to about 20 carbon atoms; $(R_3)_aZX_b$;

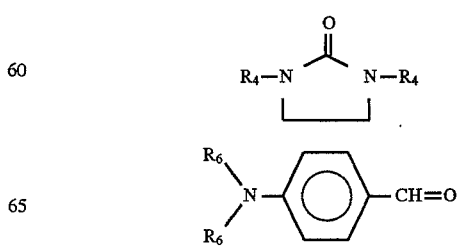

-continued

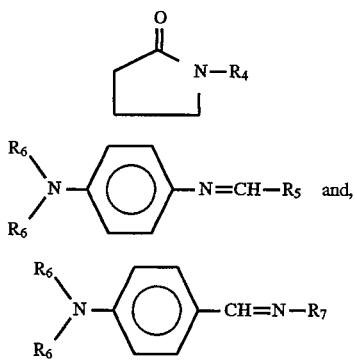

where Z is tin or silicon. It is preferred that Z is tin.

$R_3$ is an alkyl having from about 1 to about 20 carbon atoms; a cycloalkyl having from about 3 to about 20 carbon atoms; an aryl having from about 6 to about 20 carbon atoms; or, an aralkyl having from about 7 to about 20 carbon atoms. For example, $R_3$ may include methyl, ethyl, n-butyl, neophyl, phenyl, cyclohexyl or the like.

X is chlorine, bromine or iodine, "a" is from 0 to 3, and "b" is from 1 to 4; where a+b=4.

Each $R_4$ is the same or different and is an alkyl, cycloalkyl or aryl, having from about 1 to about 12 carbon atoms. For example, $R_4$ may include methyl, ethyl, nonyl, t-butyl, phenyl or the like.

$R_5$ is an alkyl, phenyl, alkylphenyl or dialkylaminophenyl, having from about 1 to about 20 carbon atoms. For example, $R_5$ may include t-butyl, 2-methyl-4-pentene-2-yl, phenyl, p-tolyl, p-butylphenyl, p-dodecylphenyl, p-diethyl-aminophenyl, p-(pyrrolidino)phenyl, and the like.

Each $R_6$ is the same or different, and is an alkyl or cycloalkyl having from about 1 to about 12 carbon atoms. Two of the $R_6$ groups may together form a cyclic group. For example, $R_6$ may include methyl, ethyl, octyl, tetramethylene, pentamethylene, cyclohexyl or the like.

$R_7$ may include alkyl, phenyl, alkylphenyl or dialkylaminophenyl, having from about 1 to about 20 carbon atoms. For example, $R_7$ may include methyl, butyl, phenyl, p-butylphenyl, p-nonylphenyl, p-dimethylaminophenyl, p-diethylaminophenyl, p-(piperidino)phenyl, or the like.

Other examples of useful modifying agents include $SnCl_4$, $(R_1)_3SnCl$, $(R_1)_2SnCl_2$, $R_1SnCl_3$, $SiCl_4$, $(R_1)_3SiCl$, $(R_1)_2SiCl_2$, $R_1SiCl_3$, carbodiimides, N-methylpyrrolidine, cyclic amides, cyclic ureas, isocyanates, Schiff bases, 4,4'-bis(diethylamino) benzophenone, and the like, where $R_1$ is as described hereinabove.

The modifying agent is added to the reaction vessel, and the vessel is agitated for about 1 to about 1000 minutes. As a result, an elastomer is produced having an even greater affinity for compounding materials such as carbon black, and hence, even further reduced hysteresis. Additional examples of modifying agents include those found in U.S. Pat. No. 4,616,069 which is herein incorporated by reference. Care should be taken to preserve the live C—Li for effective termination, such as by avoiding prolonged exposure to high temperatures or impurities such as protic acids or the like.

The polymer may be separated from the solvent by conventional techniques. These include steam or alcohol coagulation, thermal desolventization, or any other suitable method. Additionally, solvent may be removed from the resulting polymer by drum drying, extruder drying, vacuum drying or the like.

The elastomers of the present invention comprise a plurality of polymer molecules having a functional group at two or more ends. Compounds of such polymers may result in products exhibiting reduced hysteresis, which means a product having increased rebound, decreased rolling resistance and has less heat build-up when subjected to mechanical stress. Furthermore, one aspect according to the invention elastomer is formed from a plurality of polymer chains as above, and is also multifunctional wherein the polymer also carries a tin-carbon bond, such as may be derived from a modifying agent such as the terminating, coupling or linking agent discussed hereinabove.

It has also been found, as will be exemplified hereinbelow, that polymers formed using the initiator mixture of the invention, are repeatably producible in a relatively narrow range of molecular weights, such as that substantially consistently reproducible polymers are possible with a molecular weight range of about 20,000 to about 250,000.

The polymers of the present invention can be used alone or in combination with other elastomers to prepare an elastomer product such as a treadstock compound. A treadstock compound can be formed from a vulcanizable elastomeric composition of the invention polymers. A tire according to the invention may have at least a portion of its tread formed from such a treadstock compound. Compounds to form other tire structural elements, such as sidewalls, carcasses and the like, can also be advantageously made from the polymers of the present invention.

For example, the polymers according to the invention can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, Neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. When the polymers of the present invention are blended with such conventional rubbers, the amounts can vary widely such as between 10 and 99 percent by weight.

The polymers can be compounded with reinforcing agents such as carbon black in amounts ranging from about 5 to about 100 parts by weight, per 100 parts of rubber (phr), with about 5 to about 80 phr being preferred, in order to form a vulcanizable elastomeric composition. Useful carbon blacks may include any of the commonly available, commercially-produced carbon blacks but those having a surface area (EMSA) of at least 20 $m^2$/gram and more typically at least 35 $m^2$/gram up to 200 $m^2$/gram or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following TABLE I.

TABLE I

CARBON BLACKS

| ASTM Designation (D-1765-82a) | Surface Area ($m^2g$) (D-3765) |
|---|---|
| N-110 | 126 |
| N-220 | 111 |
| N-339 | 95 |
| N-330 | 83 |
| N-550 | 42 |
| N-660 | 35 |

The carbon blacks utilized in the preparation of the rubber compounds of the invention may be in pelletized form or an unpelletized flocculent mass. Preferably, for more uniform mixing, unpelletized carbon black is preferred. The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology*, 3rd ed., Wiley Interscience, N.Y. 1982, Vol. 20, pp. 365–468, particularly "Vulcanization Agents and Auxiliary Materials" pp. 390–402. Vulcanizing agents may be used alone or in combination.

Vulcanizable elastomeric compositions of the invention can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

GENERAL EXPERIMENTAL

In order to demonstrate the preparation and properties of the initiator mixture and elastomers of the present invention, a number of such initiator mixtures and elastomers were prepared. A solution of styrene and butadiene monomers in hexane was prepared and polymerized with the above described mixtures. As noted above, various techniques known in the art for carrying out anionic polymerizations may be employed without departing from the scope of the present invention.

EXAMPLE NO. 1

Preparation of Initiator Mixture 3,3,5-trimethyltetrahydroazepine (also known as trimethylhexamethyleneimine or "THMI"), was vacuum distilled from calcium hydride at approximately 75° C. at approximately 15 Torr and transferred under nitrogen to a dried, nitrogen-purged bottle. Hexamethyleneimine, "HMI", was distilled from calcium hydride and transferred under nitrogen to a dried, nitrogen-purged bottle. The mixed lithium amides HMI and THMI ("LHMI/LTHMI") were prepared by treating a mixture of 7.5 milli equivalent (meq) of a 1.16M solution of THMI in hexanes and 7.5 meq of neat HMI with 15.0 meq of a 1.67M solution of n-butyllithium in hexanes, swirling the mixture at room temperature overnight. The resulting approximately 0.9M solution was a clear, pale yellow. When either HMI or THMI alone was treated with n-butyllithium in hexanes in the absence of the second amine, cloudiness and/or precipitation occurred immediately. The ("LHMI/LTHMI") solution was stable for at least a month at room temperature. Samples were drawn from it by syringe for use in initiating polymerization.

A. Polymerization of Butadiene and Styrene with LHMI/LTHMI

A 0.9M solution of the above initiator mixture was added to a 80 percent/20 percent by weight blend of butadiene and styrene in hexanes, at a level of 1.0 meq Li/100 g monomer, and N,N,N',N'-tetramethylethylenediamine ("TMEDA") was added at 0.30 TMEDA/Li on a mole/mole basis. The mixture was agitated at 50° C. for 2.5 hr, proceeding to approximately 100 percent conversion to polymer. In practicing the invention, there is considerable leeway in the reaction times and temperatures, as well as in the reaction vessels, type of agitation, etc., used. The polymer cements then were quenched by injection with 1.5 ml of i-PrOH, treated with an antioxidant (3 ml of a mixture containing 1.6 wt percent DBPC in hexane), coagulated in i-PrOH, air-dried at room temperature, then drum-dried. Suitable characterizations were performed. The product polymer contained 20.0 percent styrene (1.5 percent block), 37.0 percent vinyl (46.3 percent vinyl if butadiene (or "BD")=100 percent), Tg −47° C., GPC(THF): $M_n$ 103582, molecular weight distribution (Mw/Mn or MWD) 1.31, raw M L/4/100=15.

B. Polymerization of Butadiene and Styrene with LHMI/LTHMI and End-linking with $SnCl_4$ The above procedure was followed exactly, except that after 1.5 hour of polymerization at 50° C., the polymerization mixture was treated with 0.8 equivalent of $SnCl_4$ per equivalent of Li charged. The product was worked up in the same manner as above. The product polymer contained 19.4 percent styrene (0.8 percent block), 39.5 percent vinyl (49 percent vinyl if BD=100 percent), Tg −45° C., GPC(THF): $M_n$ 165756, MWD 1.72, ca. 54 percent high molecular weight; raw ML/4/100=65.

Evaluation of Compounded Properties

The product polymer was compounded and tested as indicated in the test recipe shown in TABLE II, and cured 20 minutes at 165° C. Results of physical tests are reported in TABLE III hereinbelow:

TABLE II

COMPOUNDING RECIPE

| Ingredient | Mix Order | Parts per Hundred Parts Rubber | |
|---|---|---|---|
| Polymer | 1 | 100 | Masterbatch |
| Naphthenic oil | 2 | 10 | 145–155° C., |
| Carbon black, N-351 | 3 | 55 | 60 RPM |
| ZnO | 4 | 3 | |
| Antioxidant | 5 | 1 | |
| Wax blend | 6 | 2 | |
| Total Masterbatch: | | 171 | |
| Stearic acid | | 2 | Final |
| Sulfur | | 1.5 | 77–93° C., |
| Accelerator | | 1 | 40 RPM |
| Total Final: | | 175.5 | |

TABLE III

PHYSICAL TEST RESULTS, EXAMPLE NO. 1

| Example | ML/4/212 | | 1 Hz Dynastat tan δ | RING STRESS-STRAIN, R.T. | | |
|---|---|---|---|---|---|---|
| | | | | | | Percent |
| No. | (gum) | (cpd) | 50° C. | M300 | T.S. | Eb |
| 1-A | 15 | 65 | 0.098 | 2562 | 3244 | 410 |
| 1-B | 65 | 94 | 0.088 | 2673 | 3167 | 390 |

In addition, the carbon-bound rubber content of the uncured, final compounded stocks of 1-A and 1-B were 36 percent and 42 percent respectively. This indicates an enhanced interaction between the polymer and carbon black in these cases, compared to unmodified rubber, which typically exhibits 20–22 percent carbon-bound rubber, and a comparable butyllithium-initiated, Sn-linked rubber, which typically exhibits 31–33 percent carbon-bound rubber. The results of this test provide good evidence for reduced hysteresis in this polymer. The Dynastat tan δ(50° C.)=0.098 is about 50 percent below the value expected for a comparable unmodified polymer of this molecular weight, prepared using a typical alkyllithium initiator.

The carbon-bound rubber content was determined by placing a 0.4 to 0.5 grams sample of the uncured compound into 100 ml of distilled reagent toluene for two days at room temperature and without agitation. After recovering the solids, at constant weight the amount of rubber attached to carbon can be estimated since the amount of other insoluble ingredients in the original sample, (such as the carbon black) are known.

EXAMPLE NO. 2

Preparation of Initiator Mixture

Hexamethyleneimine, "HMI", was distilled and handled as described above. Pyrrolidine, "PY", was distilled from $CaH_2$ at atmospheric pressure and handled in the same manner. The mixed N-lithio salts of HMI and PY ("LHMI/LPY") were prepared by treating a mixture of 7.5 meq of a 5.45M solution of PY in hexanes and 7.5 meq of a 2.24M solution of HMI in 85:15 cyclohexane: hexanes with 15.0 meq of a 1.67M solution of n-butyllithium in hexanes, swirling the mixture at room temperature overnight. The resulting approximately 1.09M solution was a clear, light-medium yellow. When PY alone was treated with n-butyllithium in hexane or cyclohexane, in the absence of the second amine or other solubilization agent, heavy precipitation occurred almost immediately. The ("LHMI/LPY") solution was stable for at least several days at room temperature. Samples were drawn from it by syringe for use in initiating polymerization.

A. Polymerization of Butadiene and Styrene with LHMI/LPY

The 1.09M solution of the above initiator was added to a 80 percent/20 percent by weight blend of butadiene and styrene in hexanes, at a level of 1.0 meq Li/100 g monomer, and TMEDA was added at 0.30 TMEDA/Li. The mixture was agitated at 50° C. for 2.5 hours, proceeding to approximately 100 percent conversion to polymer. The polymer was worked up as described in the previous examples. The product polymer contained 20.2 percent styrene (3.3 percent block), 28.7 percent vinyl (36.0 percent vinyl if BD=100 percent), Tg –58° C., GPC(THF): $M_n$ 103302, MWD 1.60, raw ML/4/100=21.

B. Polymerization of Butadiene and Styrene with LHMI/LPY and End-linking with $SnCl_4$ The above procedure was followed exactly, except that after 1.5 hour of polymerization at 50° C., the polymerization mixture was treated with 0.8 equivalents of $SnCl_4$ per equivalents of Li charged. The product was worked up in the same manner as above. The product polymer contained 20.1 percent styrene (1.6 percent block), 35.0 percent vinyl (43.8 percent vinyl if BD=100 percent), Tg –49° C., GPC(THF): $M_n$ 145511, MWD 1.90, ca. 52 percent high molecular weight; raw ML/4/100=62.

Evaluation of Compounded Properties

Product polymer 2-B was compounded and tested as indicated in the test recipe shown in TABLE II hereinabove, and cured 20 minutes at 165° C. Results of physical tests are reported in TABLE IV hereinbelow.

TABLE IV

PHYSICAL TEST RESULTS, EXAMPLE NO. 2

| Example | ML/4/212 | | 1 Hz Dynastat tan δ | Ring Stress-Strain, R.T. | | |
|---|---|---|---|---|---|---|
| | | | | | | Percent |
| No. | (gum) | (cpd) | 50° C. | M300 | T.S. | Eb |
| 2-B | 62 | 98 | 0.101 | 2996 | 3893 | 411 |

The results of this test provided good evidence for reduced hysteresis in this polymer. The Dynastat tan δ(50° C.)=0.101 is about 48 percent below the value expected for an unmodified polymer of this molecular weight, prepared using a typical alkyllithium initiator.

EXAMPLE NO. 3

Preparation of Initiator Mixture

The mixed lithio salts of hexamethyleneimine (HMI) and dodecamethyleneimine (DDMI): "LHMI/LDDMI" were prepared by treating a mixture of 5 meq of a 1.0M solution of HMI in hexanes and 5 meq of a 1.0M solution of DDMI in hexanes with 10 meq of a 1.6M solution of n-BuLi in hexanes at room temperature with gentle agitation. The resulting approximately 0.62M medium-yellow solution was clear and stable for days. When DDMI alone was treated with n-BuLi under these conditions, heavy precipitation occurred within 16 hours. When HMI alone was treated with n-BuLi at this concentration in hexanes, precipitation was noted within a day.

Polymerization of Butadiene and Styrene with "LHMI/LDDMI" and Evaluation of the Compounded Properties of the Products The above mixture can be used to initiate polymerizations in the manner of the previous examples, using 1,3-dienes such as butadiene or mixtures of 1,3-dienes with vinylaromatic monomers, such as styrene. The resulting polymers are living and can be further reacted with functional compounds, end-linked with SnCl4, or quenched, such reactions also having been generally discussed hereinabove. When compounded with carbon black and/or other suitable fillers, the resulting compositions will exhibit reduced hysteresis, compared to compositions made from n-BuLi without the "LHMI/LDDMI" initiator mixture.

EXAMPLE NO. 4

Preparation of Initiator Mixture

The mixed lithio salts of dodecamethyleneimine (DDMI) and trimethylhexamethyleneimine(THMI): "LDDMI/

LTHMI" were prepared by treating a mixture of 10 meq of a 1.0M solution of DDMI in hexanes and 10 meq of neat THMI (1.66 ml) with 20 meq of a 1.6M solution of n-BuLi in hexanes at room temperature with gentle agitation. The resulting approximately 0.83M medium-yellow solution was hazy and stable for days. When DDMI alone was treated with n-BuLi under these conditions, heavy precipitation occurred with 16 hours. When HMI alone was treated with n-BuLi at this concentration in hexane, precipitation was noted within a day.

Polymerization of Butadiene and Styrene with "LDDMI/LTHMI" and Evaluation of the Compounded Properties of the Products The above mixture can be used to initiate polymerizations in the manner of the previous examples, using 1,3-dienes such as butadiene or mixtures of 1,3-dienes with vinylaromatic monomers, such as styrene. The resulting polymers are living and can be further reacted with functional compounds, end-liked with SnCl4, or quenched. When compounded with carbon black and/or other suitable fillers, the resulting compositions will exhibit reduced hysteresis, compared to compositions made from n-BuLi without the "LDDMI/LTHMI" initiator mixture.

A preferred method of preparing the initiators for the mixture, according to the invention, is as follows. A glass vessel, such as a small bottle containing a Teflon or glass-clad magnetic stirring bar, is dried, sealed, and purged with nitrogen. The following reagents are added at room temperature by syringe while stirring:

1. 30 mmol total of a mixture of anhydrous secondary amines in hydrocarbon solvent;
2. 30.1 mmol of alkyl lithium in hydrocarbon solvent (added by syringe at once, with stirring, while taking precaution for back-pressures).

The solution will heat and develop pressure immediately, but will soon begin to cool back down. When larger amounts of reagent are prepared, e.g. 250–300 mmol in large bottles or 0.5–1.5 mol in reactors, best results are obtained when chilled or cold water cooling is used to keep the peak reaction temperature at about 38° C. or below. The normal procedure has been to allow the mixture to stir overnight at room temperature before using. However, the reaction is essentially complete within minutes. The mixture should be clear, straw-yellow, without significant precipitation. Light-to-moderate haziness or cloudiness does not appear to affect activity. Anhydrous conditions are required. Hydrocarbon solvent solutions with less than 30 parts per million (ppm) of water give best results. Some solutions are stable for 3 or more days, and initiator reagents can be stored under positive nitrogen pressures for periods of up to several weeks or more at room temperature (25°–27° C.).

As is clear from the foregoing examples and specification disclosure, that initiator mixtures according to the present invention are useful for the anionic polymerization of diene monomers. Reproducible polymerization of such polymers within a relatively narrow molecular weight range is achieved, and the resulting polymers also exhibit good preservation of live C-Li ends, when compared to the initiators heretofore known in the art.

It is to be understood that the invention is not limited to the specific initiator reactants, monomers, modifying agents, polar coordinators or solvents disclosed herein, except as otherwise stated in the specification. Similarly, the examples have been provided merely to demonstrate practice of the subject invention and do not constitute limitations of the invention. Those skilled in the art may readily select other monomers and process conditions, according to the disclosure made hereinabove.

Thus, it is believed that any of the variables disclosed herein can readily be determined and controlled without departing from the scope of the invention herein disclosed and described. Moreover, the scope of the invention shall include all modifications and variations that fall within the scope of the attached claims.

What is claimed is:

1. An acyclic alkane soluble anionic polymerization initiator for the preparation of a polymer having reduced hysteresis characteristics, consisting essentially of a mixture comprising:

from about 90 to about 10 parts by weight of a lithio amine having the formula $A_1Li$ and from about 10 to about 90 parts by weight of at least one other lithio amine having the formula $A_2Li$;

wherein $A_1$ and $A_2$ are different and are independently selected from the group consisting of cyclic amine radicals having the formula

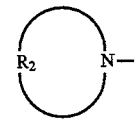

where $R_2$ is selected from the group consisting of a divalent alkylene, bicycloalkane, oxy- or N-alkylamino-alkylene group having from about 3 to about 16 methylene groups.

2. An anionic polymerization initiator, as set forth in claim 1, wherein $R_2$ includes at least six methylene groups, two of which are bridged to form a bicycloalkane radical.

3. An anionic polymerization initiator, as set forth in claim 1, wherein $A_1$ and $A_2$ are selected from the group consisting of hexamethyleneimine; 1,3,3-trimethyl-6-azabicyclo octane; pyrrolidine; piperidine; piperazine; 1-azacyclooctane; perhydroindole; azacyclotridecane; azacycloheptadecane; azacycloheptadec-9-ene; and, azacycloheptadec-8-ene.

4. A method of preparing an acyclic alkane soluble, anionic polymerization initiator for the preparation of a polymer having reduced hysteresis characteristics, comprising the steps of:

forming a solution by mixing from about 90 to 10 parts by weight of a first amine with from about 10 to 90 parts by weight of at least one other amine in an anhydrous, aprotic, acyclic alkane solvent; adding an organolithium reagent to the solution and allowing said organolithium reagent to react with said amines;

wherein each of said amines are selected from the group consisting of cyclic amines having the formula

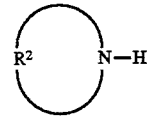

where $R_2$ is selected from the group consisting of a divalent alkylene, bicycloalkane, oxy- or N-alkylamino-alkylene group having from about 3 to about 16 methylene groups; and, wherein said organolithium reagent has the formula RLi where R is selected from the group consisting of alkyls, cycloalkyls, alkenyls, aryls and aralkyls having from 1 to about 20 carbon atoms and short chain length low molecular weight polymers of diolefin and vinyl aryl monomers having up to about 25 units.

* * * * *